(12) United States Patent
Steffensmeier

(10) Patent No.: US 8,167,888 B2
(45) Date of Patent: May 1, 2012

(54) TIBIAL SPACER BLOCKS AND FEMORAL CUTTING GUIDE

(75) Inventor: Scott Steffensmeier, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 940 days.

(21) Appl. No.: 10/912,988

(22) Filed: Aug. 6, 2004

(65) Prior Publication Data
US 2006/0036257 A1 Feb. 16, 2006

(51) Int. Cl.
*A61B 17/58* (2006.01)
*A61B 17/60* (2006.01)
*A61F 2/00* (2006.01)
*A61F 5/00* (2006.01)
*A61F 2/46* (2006.01)

(52) U.S. Cl. .......................... 606/88; 606/86 R; 606/87

(58) Field of Classification Search ................. 606/102, 606/86 R, 87–90; 623/20.14–20.15, 20.32–20.35, 623/23.25; 33/511, 512; D24/140
See application file for complete search history.

(56) References Cited

U.S. PATENT DOCUMENTS

| | | | |
|---|---|---|---|
| 309,709 A * | 12/1884 | Genese | 433/149 |
| 2,697,433 A | 12/1954 | Zehnder | |
| 3,532,088 A | 10/1970 | Fiore | |
| 4,211,228 A * | 7/1980 | Cloutier | 606/102 |
| 4,349,018 A | 9/1982 | Chambers | |
| 4,457,307 A | 7/1984 | Stillwell | |
| 4,524,766 A | 6/1985 | Petersen | |
| 4,566,448 A | 1/1986 | Rohr, Jr. | |
| 4,566,466 A * | 1/1986 | Ripple et al. | 606/102 |
| 4,567,886 A | 2/1986 | Petersen | |
| 4,574,794 A | 3/1986 | Cooke et al. | |
| 4,646,729 A | 3/1987 | Kenna et al. | |
| 4,738,253 A | 4/1988 | Buechel et al. | |
| 4,759,350 A | 7/1988 | Dunn et al. | |
| 4,825,857 A | 5/1989 | Kenna | |
| 4,841,975 A | 6/1989 | Woolson | |
| 4,938,762 A | 7/1990 | Wehrli | |
| 4,952,213 A | 8/1990 | Bowman et al. | |
| 5,002,547 A | 3/1991 | Poggie et al. | |
| 5,007,936 A | 4/1991 | Woolson | |
| 5,037,423 A * | 8/1991 | Kenna | 606/88 |
| 5,116,338 A | 5/1992 | Walker | |
| 5,122,144 A | 6/1992 | Bert | |

(Continued)

FOREIGN PATENT DOCUMENTS

DE  20202615 U1  6/2002

(Continued)

*Primary Examiner* — Thomas C. Barrett
*Assistant Examiner* — Christine Nelson
(74) *Attorney, Agent, or Firm* — Faegre Baker Daniels

(57) ABSTRACT

The present invention relates to one or more tibial spacer blocks used during knee arthroplasty, each configured to be temporarily positioned upon a resected proximal portion of a tibia (essentially mimicking the tibial component of the knee prosthesis), for performing a range of motion analysis and for checking flexion and extension gaps prior to cutting the distal or posterior femur. Preferably, the spacer blocks each include an attachment arrangement configured and arranged to mate with a complementary attachment arrangement of an alignment tower and/or a femoral cutting guide. The alignment tower, which is configured to be used with an alignment rod, is used for verifying the alignment of the limb's mechanical axis when the spacer block is positioned between the tibia and the femur. The femoral cutting guide is used for guiding a cutting member into proper orientation for resecting a distal or posterior portion of a femur.

18 Claims, 11 Drawing Sheets

U.S. PATENT DOCUMENTS

| | | | |
|---|---|---|---|
| 5,213,112 A | | 5/1993 | Niwa et al. |
| 5,228,459 A | * | 7/1993 | Caspari et al. ............... 128/898 |
| 5,230,338 A | | 7/1993 | Allen et al. |
| 5,234,433 A | | 8/1993 | Bert |
| 5,251,127 A | | 10/1993 | Raab |
| 5,275,603 A | | 1/1994 | Ferrante et al. |
| 5,305,203 A | | 4/1994 | Raab |
| 5,306,276 A | | 4/1994 | Johnson et al. |
| 5,342,367 A | | 8/1994 | Ferrante et al. |
| 5,342,368 A | | 8/1994 | Petersen |
| 5,344,423 A | | 9/1994 | Dietz et al. |
| 5,364,401 A | | 11/1994 | Ferrante et al. |
| 5,364,402 A | | 11/1994 | Mumme et al. |
| 5,368,552 A | | 11/1994 | Williamson et al. |
| 5,445,640 A | | 8/1995 | Johnson et al. |
| 5,451,228 A | | 9/1995 | Johnson et al. |
| 5,458,645 A | | 10/1995 | Bertin |
| 5,474,559 A | | 12/1995 | Bertin et al. |
| 5,484,446 A | | 1/1996 | Burke et al. |
| 5,486,180 A | | 1/1996 | Dietz et al. |
| 5,514,139 A | | 5/1996 | Goldstein et al. |
| 5,514,143 A | | 5/1996 | Bonutti et al. |
| 5,520,695 A | * | 5/1996 | Luckman ................ 606/88 |
| 5,527,316 A | | 6/1996 | Stone et al. |
| 5,540,696 A | | 7/1996 | Booth et al. |
| 5,551,429 A | | 9/1996 | Fitzpatrick et al. |
| 5,562,674 A | | 10/1996 | Stalcup et al. |
| 5,593,411 A | | 1/1997 | Stalcup et al. |
| 5,597,379 A | | 1/1997 | Haines et al. |
| 5,601,563 A | | 2/1997 | Burke et al. |
| 5,611,802 A | | 3/1997 | Samuelson et al. |
| 5,628,750 A | | 5/1997 | Whitlock et al. |
| 5,643,272 A | | 7/1997 | Haines |
| 5,649,928 A | | 7/1997 | Grundei |
| 5,681,316 A | | 10/1997 | DeOrio et al. |
| 5,681,320 A | | 10/1997 | McGuire |
| 5,682,886 A | | 11/1997 | Delp et al. |
| 5,683,397 A | | 11/1997 | Vendrely et al. |
| 5,688,280 A | | 11/1997 | Booth, Jr. |
| 5,704,941 A | | 1/1998 | Jacober et al. |
| 5,735,904 A | * | 4/1998 | Pappas .................. 606/86 R |
| 5,743,915 A | | 4/1998 | Bertin et al. |
| 5,755,803 A | | 5/1998 | Haines et al. |
| 5,776,201 A | | 7/1998 | Colleran et al. |
| 5,788,700 A | | 8/1998 | Morawa et al. |
| 5,800,438 A | | 9/1998 | Tuke et al. |
| 5,810,827 A | | 9/1998 | Haines et al. |
| 5,824,085 A | | 10/1998 | Sahay et al. |
| 5,860,980 A | | 1/1999 | Axelson et al. |
| 5,871,018 A | | 2/1999 | Delp et al. |
| 5,879,354 A | | 3/1999 | Haines et al. |
| 5,904,691 A | | 5/1999 | Barnett et al. |
| 5,911,723 A | | 6/1999 | Ashby et al. |
| 5,921,992 A | | 7/1999 | Costales et al. |
| 5,995,738 A | | 11/1999 | DiGioia, III et al. |
| 6,002,859 A | | 12/1999 | DiGioia, III et al. |
| 6,022,377 A | * | 2/2000 | Nuelle et al. .................. 606/90 |
| 6,033,415 A | | 3/2000 | Mittelstadt et al. |
| 6,051,016 A | | 4/2000 | Mesaros et al. |
| 6,056,754 A | | 5/2000 | Haines et al. |
| 6,077,270 A | | 6/2000 | Katz |
| 6,090,114 A | | 7/2000 | Matsuno et al. |
| 6,113,639 A | * | 9/2000 | Ray et al. .................. 623/17.16 |
| 6,167,145 A | | 12/2000 | Foley et al. |
| 6,197,064 B1 | | 3/2001 | Haines et al. |
| 6,267,762 B1 | | 7/2001 | Millard et al. |
| 6,285,902 B1 | | 9/2001 | Kienzle, III et al. |
| 6,296,646 B1 | | 10/2001 | Williamson |
| 6,368,310 B1 | * | 4/2002 | Bemis et al. .................. 604/319 |
| 6,396,939 B1 | | 5/2002 | Hu et al. |
| 6,402,762 B2 | | 6/2002 | Hunter et al. |
| 6,430,434 B1 | | 8/2002 | Mittelstadt |
| 6,450,978 B1 | | 9/2002 | Brosseau et al. |
| 6,475,228 B1 | | 11/2002 | Mesaros et al. |
| 6,477,400 B1 | | 11/2002 | Barrick |
| 6,478,799 B1 | | 11/2002 | Williamson |
| 6,490,467 B1 | | 12/2002 | Bucholz et al. |
| 6,503,254 B2 | | 1/2003 | Masini |
| 6,514,259 B2 | | 2/2003 | Picard et al. |
| 6,551,325 B2 | | 4/2003 | Neubauer et al. |
| 6,554,837 B1 | | 4/2003 | Hauri et al. |
| 6,575,980 B1 | | 6/2003 | Robie et al. |
| 6,595,997 B2 | | 7/2003 | Axelson, Jr. et al. |
| 6,632,225 B2 | | 10/2003 | Sanford et al. |
| 6,673,077 B1 | * | 1/2004 | Katz ................................. 606/88 |
| 6,685,711 B2 | | 2/2004 | Axelson, Jr. et al. |
| 6,695,848 B2 | | 2/2004 | Haines |
| 6,712,824 B2 | | 3/2004 | Millard et al. |
| 6,859,661 B2 | | 2/2005 | Tuke |
| 6,932,823 B2 | | 8/2005 | Grimm et al. |
| 7,029,477 B2 | | 4/2006 | Grimm |
| 7,094,241 B2 | | 8/2006 | Hodorek et al. |
| 7,201,755 B2 | | 4/2007 | Faoro |
| 7,235,080 B2 | | 6/2007 | Hodorek |
| 7,335,206 B2 | | 2/2008 | Steffensmeier et al. |
| 7,371,240 B2 | | 5/2008 | Pinczewski et al. |
| 2002/0068942 A1 | | 6/2002 | Neubauer et al. |
| 2002/0133160 A1 | | 9/2002 | Axelson, Jr. et al. |
| 2002/0133162 A1 | | 9/2002 | Axelson, Jr. et al. |
| 2002/0133163 A1 | | 9/2002 | Axelson, Jr. et al. |
| 2002/0133164 A1 | | 9/2002 | Williamson |
| 2002/0198530 A1 | | 12/2002 | Sanford |
| 2003/0069585 A1 | | 4/2003 | Axelson, Jr. et al. |
| 2003/0069591 A1 | | 4/2003 | Carson et al. |
| 2003/0100906 A1 | | 5/2003 | Rosa et al. |
| 2003/0130665 A1 | * | 7/2003 | Pinczewski et al. ............ 606/88 |
| 2003/0216741 A1 | | 11/2003 | Sanford et al. |
| 2003/0225413 A1 | | 12/2003 | Sanford et al. |
| 2003/0233149 A1 | | 12/2003 | Hodorek |
| 2004/0039396 A1 | | 2/2004 | Couture et al. |
| 2004/0097951 A1 | * | 5/2004 | Steffensmeier ............... 606/102 |
| 2004/0102785 A1 | | 5/2004 | Hodorek |
| 2004/0122305 A1 | | 6/2004 | Grimm et al. |
| 2004/0152955 A1 | | 8/2004 | McGinley et al. |
| 2004/0153062 A1 | | 8/2004 | McGinley et al. |
| 2004/0249387 A1 | | 12/2004 | Faoro |
| 2005/0070910 A1 | | 3/2005 | Keene |
| 2005/0143746 A1 | * | 6/2005 | Steffensmeier et al. ........ 606/88 |
| 2005/0182415 A1 | | 8/2005 | Steffensmeier et al. |
| 2005/0203528 A1 | | 9/2005 | Couture et al. |
| 2005/0203541 A1 | | 9/2005 | Steffensmeier et al. |
| 2006/0030855 A1 | | 2/2006 | Haines |
| 2006/0036257 A1 | | 2/2006 | Steffensmeier et al. |
| 2006/0149276 A1 | | 7/2006 | Grimm |
| 2006/0189998 A1 | | 8/2006 | Rasmussen |
| 2006/0195111 A1 | | 8/2006 | Couture |
| 2006/0217734 A1 | | 9/2006 | Sanford et al. |
| 2006/0247647 A1 | | 11/2006 | Hodorek et al. |
| 2007/0173854 A1 | | 7/2007 | Berger |

FOREIGN PATENT DOCUMENTS

| | | |
|---|---|---|
| DE | 20303498 U1 | 7/2003 |
| EP | 0104732 A1 | 4/1984 |
| EP | 2648699 A1 | 12/1990 |
| EP | 00709061 A1 | 5/1996 |
| EP | 00809969 B1 | 10/2002 |
| EP | 0839501 B1 | 3/2003 |
| EP | 1579812 A1 | 9/2005 |
| EP | 1424042 B1 | 3/2007 |
| FR | 2679766A1 A2 | 2/1993 |
| FR | 2776176 A1 | 9/1999 |
| FR | 2819168 A1 | 7/2002 |
| WO | WO01/66021 A1 | 9/2001 |
| WO | WO01/85038 A1 | 11/2001 |
| WO | WO2004/017842 A2 | 3/2004 |
| WO | WO2004/019792 A1 | 3/2004 |

* cited by examiner

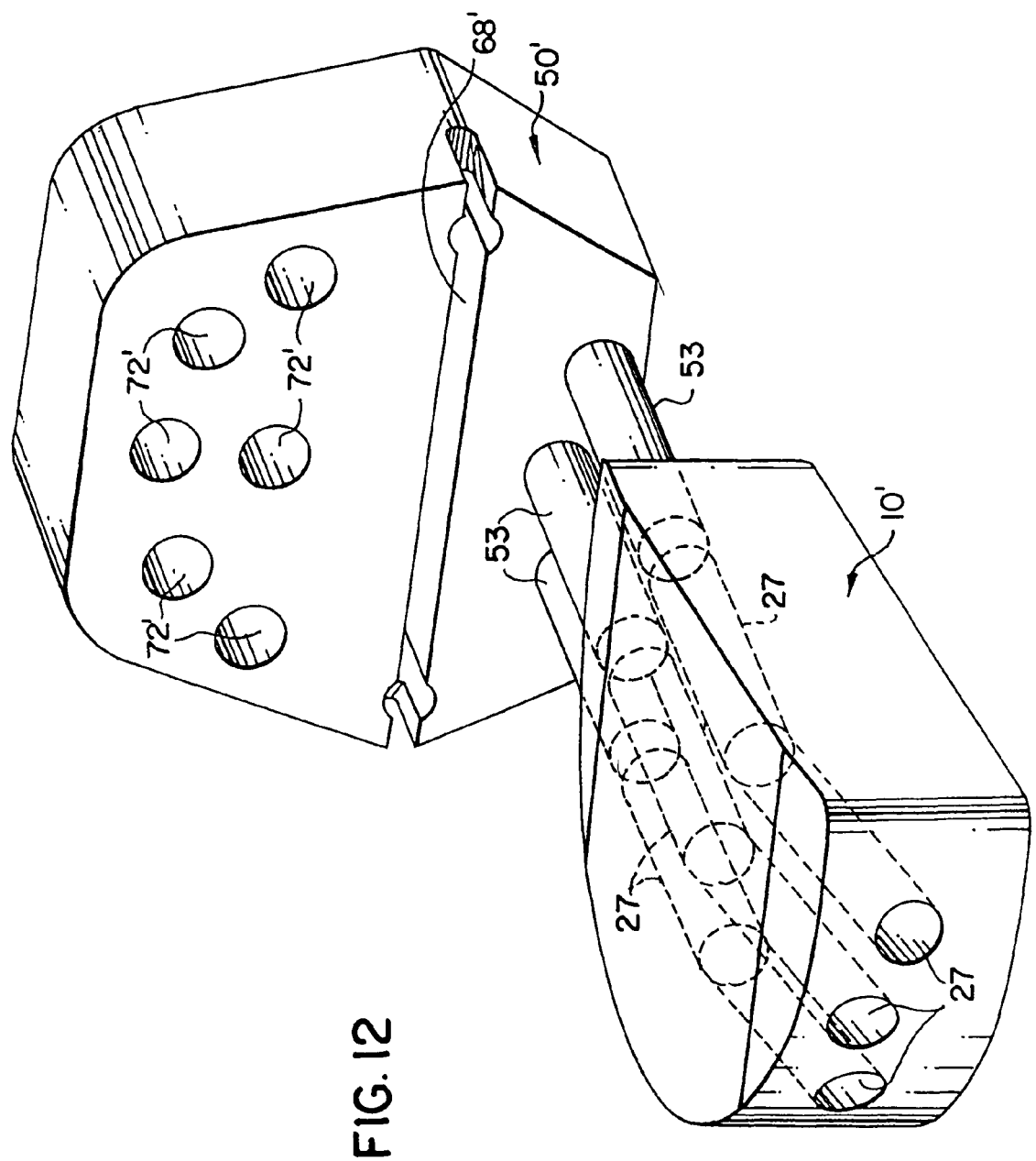

TIBIAL SPACER BLOCKS AND FEMORAL CUTTING GUIDE

The present invention relates generally to one or more components used during knee arthroplasty, where the component(s) are used for: performing a range of motion analysis and verifying the flexion and extension gaps between the femur and tibia; verifying the alignment of the femur relative to the mechanical axis; and/or guiding a cutter during resection of the distal femur and/or the posterior femur. More particularly, the present invention relates to one or more tibial spacer blocks, each configured to be temporarily positioned upon a resected proximal portion of a tibia (essentially mimicking the tibial component of the knee prosthesis), for performing a range of motion analysis and for checking flexion and extension gaps prior to cutting the distal femur and/or the posterior femur. Preferably, the spacer blocks each include an attachment arrangement configured and arranged to mate with a complementary attachment arrangement of an alignment tower and/or a femoral cutting guide. The concept of the present invention can be applied to many different types of arthroplasty, such as, for example, Unicompartmental Knee Arthroplasty (UKA) and Total Knee Arthroplasty (TKA).

Throughout this application various positional terms—such as distal, proximal, medial, lateral, anterior and posterior—will be used in the customary manner when referring to the human anatomy. More specifically, "distal" refers to the area away from the point of attachment to the body, while "proximal" refers to the area near the point of attachment the body. For example, the proximal femur refers to the portion of the femur near the hip, while the distal femur refers to the portion of the femur near the tibia. The terms "medial" and "lateral" are also essentially opposites, where "medial" refers to something situated closer to the middle of the body, while "lateral" refers to something situated closer to the left side or the right side of the body (than to the middle of the body). Finally, with regard to anterior and posterior, "anterior" refers to something situated closer to the front of the body and "posterior" refers to something situated closer to the rear of the body.

Also, the term "mechanical axis" of the femur refers to an imaginary line drawn from the center of the femoral head to the center of the distal femur at the knee and the term "anatomic axis" of the femur refers to an imaginary line drawn the middle of the femoral shaft (see FIG. 6 for examples of the mechanical axis 54 and the anatomic axis 56). The angle between the mechanical axis and the anatomic axis is generally approximately 6°.

The present invention provides an alternative approach to known methods and devices used for guiding the cutting blade for cutting the distal femur or the posterior femur during knee arthroplasty, as well as providing components for checking flexion and extension gaps and defining the amount of limb correction, all prior to cutting the distal femur. For example, one known method of guiding the cutter for cutting the distal femoral condyle (or condyles) uses an intramedullary femoral resection guide (that includes a rod seated within a hole drilled into the distal femur) upon which a distal femoral resector block is fixed, via a post and a pin (which pin is used to select the desired angle of limb correction). However, when using such an intramedullary femoral resection guide, a hole must be drilled into the distal femur to receive the rod of the guide. Additionally, the selected varus/valgus of the particular condyle can only be chosen from a set of predetermined angles provided on the intramedullary femoral resection guide (such as the angles 2°, 4°, 6°, and 8°), with no provisions for other angles, or half angles. Further, such intramedullary femoral resection guides do not provide an associated, attachable device that allows, prior to cutting the distal femur, for a range of motion analysis and for verification of the flexion and extension gaps. Similar problems are also encountered with present methods for cutting the posterior femur as well.

SUMMARY OF THE INVENTION

In one embodiment, the present invention includes a spacer block, or a plurality of blocks of different thicknesses, that are configured to be temporarily positioned upon a resected proximal portion of a tibia, where the spacer block essentially mimics the shape, in the thickness direction (i.e., the distal/proximal direction), of the tibial component of the knee joint prosthesis intended to be implanted. The spacer block can then be used when performing a range of motion analysis, and to check the flexion and extension gaps (of any flexion angle) prior to femoral cutting. This embodiment of the spacer block is also configured to cooperate with an alignment tower, for defining the amount of limb correction, and/or to cooperate with a femoral cutting guide, for aligning a cutting blade used to cut the distal femoral condyle (or condyles) to receive the femoral component of the knee joint prosthesis. The present invention can also be used for cutting the posterior femur by making the cut with the leg in flexion.

More specifically, the present invention provides a spacer block intended to be temporarily positioned upon a resected proximal portion of a tibia during knee arthroplasty. The spacer block preferably includes a main body portion and an attachment arrangement. The main body portion has a thickness defined between substantially parallel distal and proximal surfaces, where the thickness is approximately equal to a corresponding thickness of a tibial component of a knee joint prosthesis. The attachment arrangement is preferably provided on an anterior side of the main body portion, and is configured and arranged to mate with a complementary attachment arrangement of at least one of a femoral cutting guide and an alignment tower.

Additionally, another aspect of the present invention relates to a femoral cutting guide intended to be used during knee arthroplasty, after resection of a tibia, for guiding a cutting member into proper orientation for resecting a distal portion of a femur. The cutting guide preferably includes a slot configured and arranged to receive the cutting member intended to resect a portion of the femur; and an attachment arrangement configured and arranged to mate with a complementary attachment arrangement on a spacer block.

Yet another aspect of the present invention relates to a system of components used during knee arthroplasty, after resection of a tibia, for guiding a cutting member into proper orientation for resecting a portion of a femur. The system preferably includes a femoral cutting guide and a plurality of spacer blocks of different thicknesses. One embodiment of the femoral cutting guide includes a slot configured and arranged to receive the cutting member intended to resect a portion of the femur. In this embodiment of the spacer blocks are each configured to be temporarily positioned upon a resected proximal portion of a tibia during knee arthroplasty, with each of the spacer blocks including a main body portion and an attachment arrangement. The thickness of each main body portion is defined between substantially parallel distal and proximal surfaces, where the thickness of the main body portion of a particular spacer block is approximately equal to a corresponding thickness of a tibial component of a knee joint prosthesis. The attachment arrangement is preferably provided on an anterior side of the main body portion, and the arrangement is preferably configured and arranged to mate with a complementary attachment arrangement on the femoral cutting guide.

The system may also include an alignment tower and an alignment rod. The alignment tower preferably includes a second complementary attachment arrangement, of a similar configuration to the complementary attachment arrangement of the femoral cutting guide. The second complementary attachment arrangement is also configured and arranged to mate with the attachment arrangement of each of the spacer blocks. The alignment rod is preferably configured to be inserted into a hole within the alignment tower, wherein the alignment rod is used for checking the alignment of the limb.

BRIEF DESCRIPTION OF THE SEVERAL VIEWS OF THE DRAWINGS

Preferred embodiments of the present invention are described herein with reference to the drawings wherein:

FIG. 12 is a perspective view of a spacer block and femoral cutting guide of a second embodiment of the present invention;

FIG. 13A is a perspective view and FIG. 13B is a side view showing (in hidden lines) how the attachment arrangements mate with each other;

FIG. 14A is a perspective view and FIG. 14B is a side view showing (in hidden lines) how the attachment arrangements mate with each other;

FIG. 15A is a perspective view and FIG. 15B is a side view showing (in hidden lines) how the attachment arrangements mate with each other.

DETAILED DESCRIPTION OF THE INVENTION

Figure 4:
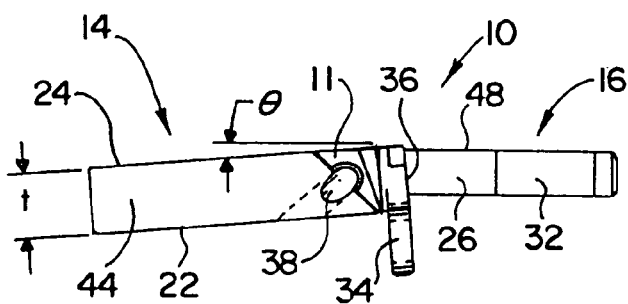
FIG. 4 is a side view of the spacer block of FIG. 1.
Figure 5:
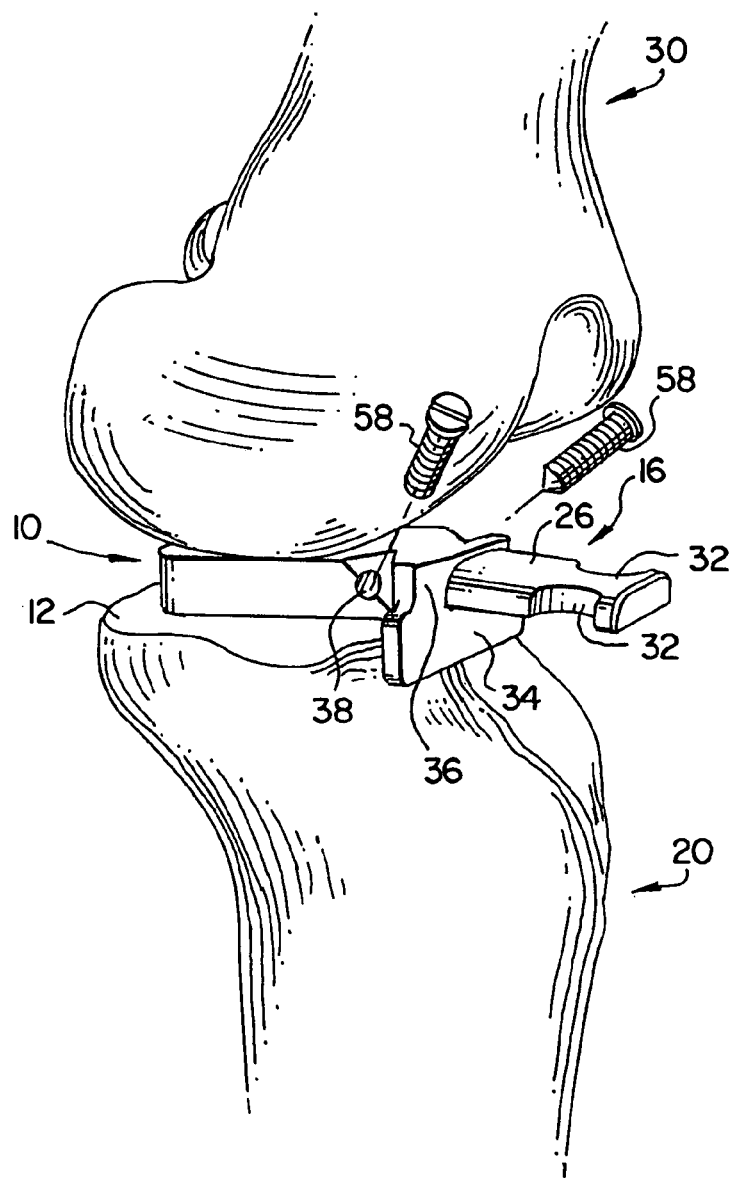
FIG. 5 is a view of the spacer block of FIG. 1 shown in position between a femur and a tibia.

Turning now to FIGS. 1-5, one embodiment of the present spacer block 10 will be shown and described, with FIG. 5 showing spacer block 10 in position between a tibia 20 and a femur 30. As mentioned above, and as shown in FIG. 5, spacer block 10 is configured to be temporarily positioned upon a resected proximal surface 12 of a tibia 20 during knee arthroplasty. Once in position, a range of motion analysis can be performed, as well as verification of the flexion and extension gaps, all prior to cutting either the distal portion of the femur or the posterior portion of the femur. Further, this embodiment of the spacer block 10 also provides an arrangement for attaching either, or both, an alignment tower (such as tower 40 of FIG. 7) and/or a femoral cutting guide (such as cutting guide 50 of FIG. 10).

Spacer block 10 preferably includes two main components: a main body portion 14 and an attachment arrangement 16. The main body portion is defined between a distal surface 22 and a proximal surface 24. As best shown in FIG. 4, the distal surface 22 is preferably substantially parallel to the proximal surface 24. Accordingly, in the thickness direction (i.e., the distal/proximal direction) the body portion 14 mimics the shape of a tibial component of a knee joint prosthesis. Further, a plurality of spacer blocks 10 are preferably provided with different thicknesses "t" (FIG. 4), whereby the different thicknesses correspond to the different thicknesses of the different tibial components. For example, where the tibial component of a knee joint prosthesis is provided in thicknesses of 8 mm, 10 mm, 12 mm and 14 mm, the spacer block 10 should be provided with thicknesses "t" of 8 mm, 10 mm, 12 mm and 14 mm. If desired, modular attachments (not shown) of different thicknesses can also be provided to increase the thickness of a block. For example, a 2 mm thick modular attachment can be added to a 10 mm thick spacer block to result in a 12 mm thick spacer block assembly. Of course, the sample thickness dimensions provided here (as well as any other dimensions discussed in this application) are provided by way of example only, and other dimensions are also contemplated as being within the scope of the invention.

Figure 1:
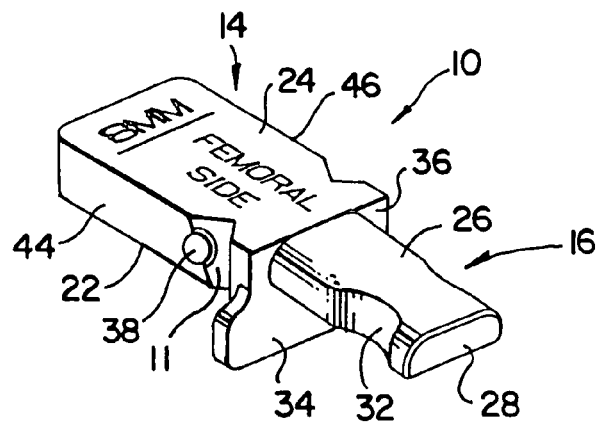
FIG. 1 is a proximal perspective view, shown from the anterior side, of a first embodiment of the present spacer block.
Figure 2:
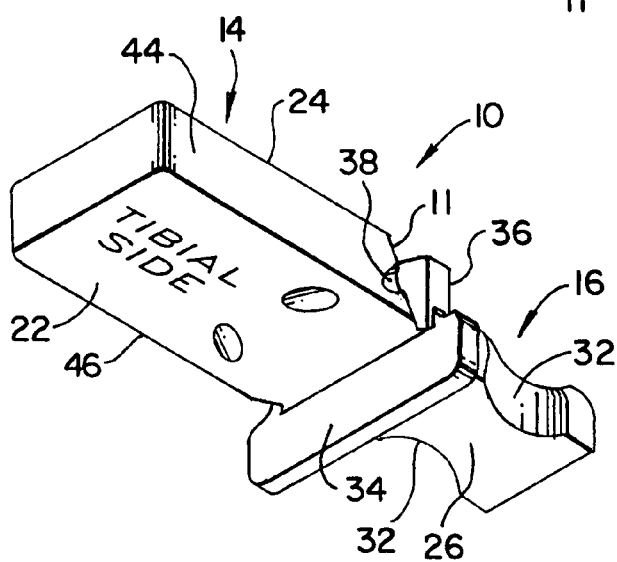
FIG. 2 is a distal perspective view, shown from the posterior side, of the spacer block of FIG. 1.
Figure 3:
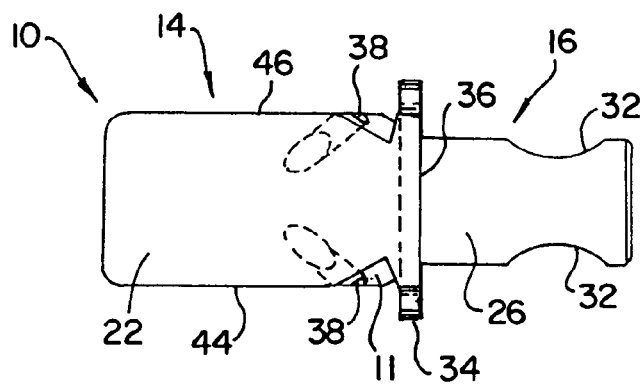
FIG. 3 is a proximal view of the spacer block of FIG. 1.

The spacer block of the present invention preferably includes markings designating the thickness of the main body portion, such as the 8 mm marking shown in FIG. 1. Additional markings are also preferably provided to designate the tibial side and femoral side of the spacer block, such as shown in FIGS. 1 and 2.

One example of an attachment arrangement 16 of the spacer block 10 is shown in FIGS. 1-5. In the embodiment shown in the figures, the attachment arrangement includes a projection 26 of a generally D-shaped cross-section (which D-shaped cross-section can be seen by referring to end portion 28 shown in FIG. 1). By utilizing such a cross-section for projection 26, inverted attachment of other components (such as alignment tower 40 or femoral cutting guide 50) to the projection 26 is prevented because the corresponding apertures on the tower or the cutting guide are also generally D-shaped in cross-section (such as aperture 42 of the tower 40 of FIG. 7 and aperture 52 of the cutting guide 50 of FIG. 8).

Instead of utilizing a generally D-shaped cross-sectional projection (and apertures of corresponding cross-section), other shaped cross-sections are also contemplated as being within the scope of the invention. Preferably, if the D-shaped cross-section is not used, another non-circular cross-section is used in order to still prevent inverted attachment of the tower or the cutting guide to the spacer block. Of course, if the inversion prevention feature is not desired, a projection and a corresponding aperture of circular cross-sections may be used. Further, instead of using attachment arrangements including only a single projection and a single aperture, it is also contemplated that multiple projections and multiple corresponding apertures could also be used (such as in the embodiment of FIG. 12). In such instances, the projections and apertures could be of non-circular cross-sections if desired, or they could also be of circular cross-sections, as long as the positions and/or sizes of the projections/apertures prevents inverted attachment, if such a feature is desired. Further, it is also contemplated that the position of the projection(s) and aperture(s) could be reversed, with the projection(s) provided on the alignment tower and the cutting guide, and the aperture(s) provided on the spacer block (such as in the embodiments of FIGS. 12-16).

Referring back to the embodiment of FIGS. 1-5, projection 26 also functions as a handle for moving the spacer block into and out of position, in addition to performing the attachment function. In this embodiment, the projection 26 preferably includes two concave gripping areas 32, which facilitate gripping of the spacer block 10 between two fingers.

In order to help maintain the spacer block 10 in position upon the resected proximal surface 12 of the tibia 20, as shown in FIG. 5, an anterior stop 34 is preferably provided. As shown in FIGS. 1-5, anterior stop 34 projects from the distal surface 22 of the spacer block, near the anterior side 36 of the main body portion 14.

In order to further help in maintaining the spacer block 10 in position, the main body portion 14 preferably includes at least one aperture configured to receive a pin (either threaded or unthreaded) for pinning the spacer block in position. In this embodiment, a pair of apertures 38 are preferably provided. Preferably, the apertures 38 each extend from one of the side walls 44 or 46 to the distal surface 22 of the main body portion 14. By placing the apertures 38 in these locations, the pins can be inserted or removed without being hindered by the distal femur, and the pins do not block usage of the spacer block or any other components attached to the spacer block.

In the embodiment of FIGS. 1-5, both the anterior stop 34 and at least one aperture/pin combination are used together in order to maintain the spacer block in the desired position. However, it is contemplated that either the anterior stop or at least one aperture/pin combination may be used alone. Further, it is also contemplated that different structures or systems for temporarily positioning the spacer block in position may be used either along with the anterior stop and/or the aperture pin combination, or in place of one or more of these structures or systems.

Referring to FIG. 4, it can be seen that in this embodiment, the proximal surface 24 of the main body portion 14 is not parallel with the proximal surface 48 of projection 26. Instead, an angle θ is defined between proximal surface 24 and a line extending from surface 48 (it should be noted that the same angle θ would also be provided between surface 48 and a line extending from surface 24). In this embodiment, angle θ is preferably approximately 5°. An angle θ of approximately 5° accounts for the 5° posterior tibial slope of resected proximal surface 12 (FIG. 5) desired in most patients, while maintaining the projection 26 normal to the mechanical axis 54 (see FIG. 6 for an example of mechanical axis 54). The 5° posterior tibial slope is midway between the typical range for most patients of between 3° and 7°, and it is also midway between the extremes of the 0° to 10° found in some patients. Of course, if desired, the angle θ may be set to a value other than 5°.

Turning now to FIG. 5, the positioning and use of the spacer block 10 will be described. Prior to placing the spacer block of the present invention in position, the proximal surface of the tibia 20 must be resected, using any desired method. After resection, the resulting resected proximal surface 12 created will be relatively smooth and properly aligned to receive the tibial component of the selected type of knee joint prosthesis (once additional preparation steps of the tibia are completed, such as drilling spaces to receive the pegs of the implant). However, prior to implanting the tibial component, spacer block 10 is temporarily seated upon the resected proximal surface 12 of the tibia. The spacer block 10 used will be of the same thickness as the tibial component intended to be implanted, in order for the spacer block to mimic the tibial component during analysis. Thus, a spacer block 10 of the appropriate thickness is chosen to be the same as the thickness of the tibial component selected. The spacer block 10 of the selected thickness is seated upon resected surface 12, and moved in the posterior direction, until anterior stop 34 contacts the anterior surface of the proximal portion of the tibia 20.

In the example shown in FIG. 5, the medial condyle of the left leg is damaged, and will be removed in a Unicompartmental Knee Arthroplasty (UKA) procedure. Accordingly, the spacer block 10 is positioned distal of the femoral medial condyle. Of course, if the lateral femoral condyle were being removed, the spacer block would be placed distal of the lateral femoral condyle. Regardless of whether the lateral or medial condyle is being removed, and regardless of whether it is on the right leg or the left leg, the same spacer block 10 can be used because each of the spacer blocks of a particular thickness has been designed for universal application.

Further, if both lateral and medial condyles are being removed, such as for a Total Knee Arthroplasty (TKA) procedure, the same spacer block may be used twice (once for one condyle, and then, repositioned for the other condyle or simultaneously with two condyles). In the alternative, a spacer block of a width (in the medial/lateral direction) that is approximately double that of the embodiment shown in FIGS. 1-5 may also be used, such that a single spacer block (not shown) can be seated distal of both the lateral and medial condyles at the same time.

When the spacer block 10 is properly positioned between the appropriate condyle and the resected proximal surface 12 of the tibia 20, a pin 58 is inserted into each of the apertures 38. As mentioned above, pins 58 may be threaded or not threaded, as long as they are of a configuration that can be securely inserted into the proximal tibia, as well as being easily removable when the spacer block needs to be removed. The combination of the pins 58 and the anterior projection 26 maintain the spacer block 10 in position upon the resected proximal surface 12.

After the spacer block 10 is secured in position, the tibia can be moved to perform a range of motion analysis, and the flexion and extension gaps can be checked. If it is determined that a different thickness of tibial component is needed, the spacer block can be replaced with another spacer block of an appropriate thickness that corresponds to the new thickness of the tibial component, and the range of motion analysis can be performed again.

Figure 6:
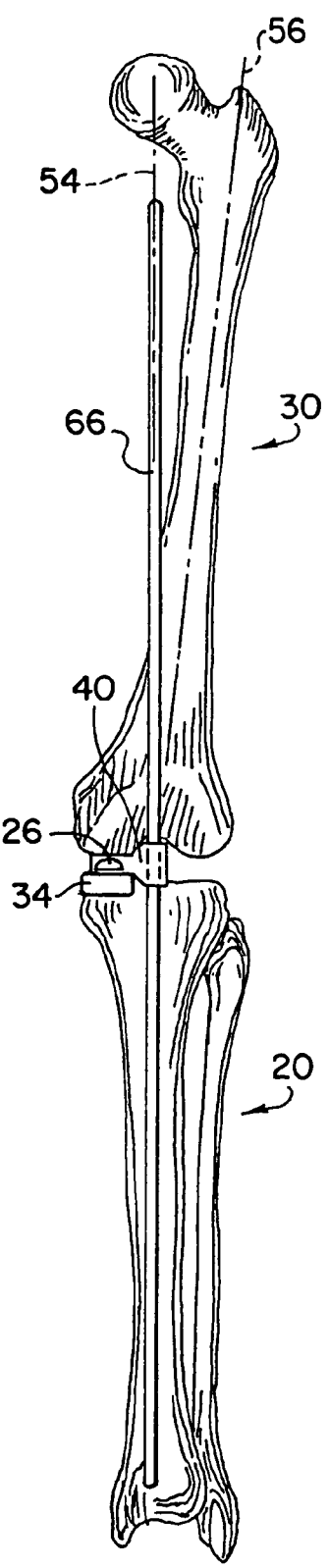
FIG. 6 is a view of the spacer block of FIG. 1, shown in position between a femur and a tibia and with an alignment tower attached, and also showing the anatomic axis and the mechanical axis of the femur, and the mechanical axis of the limb.
Figure 7:
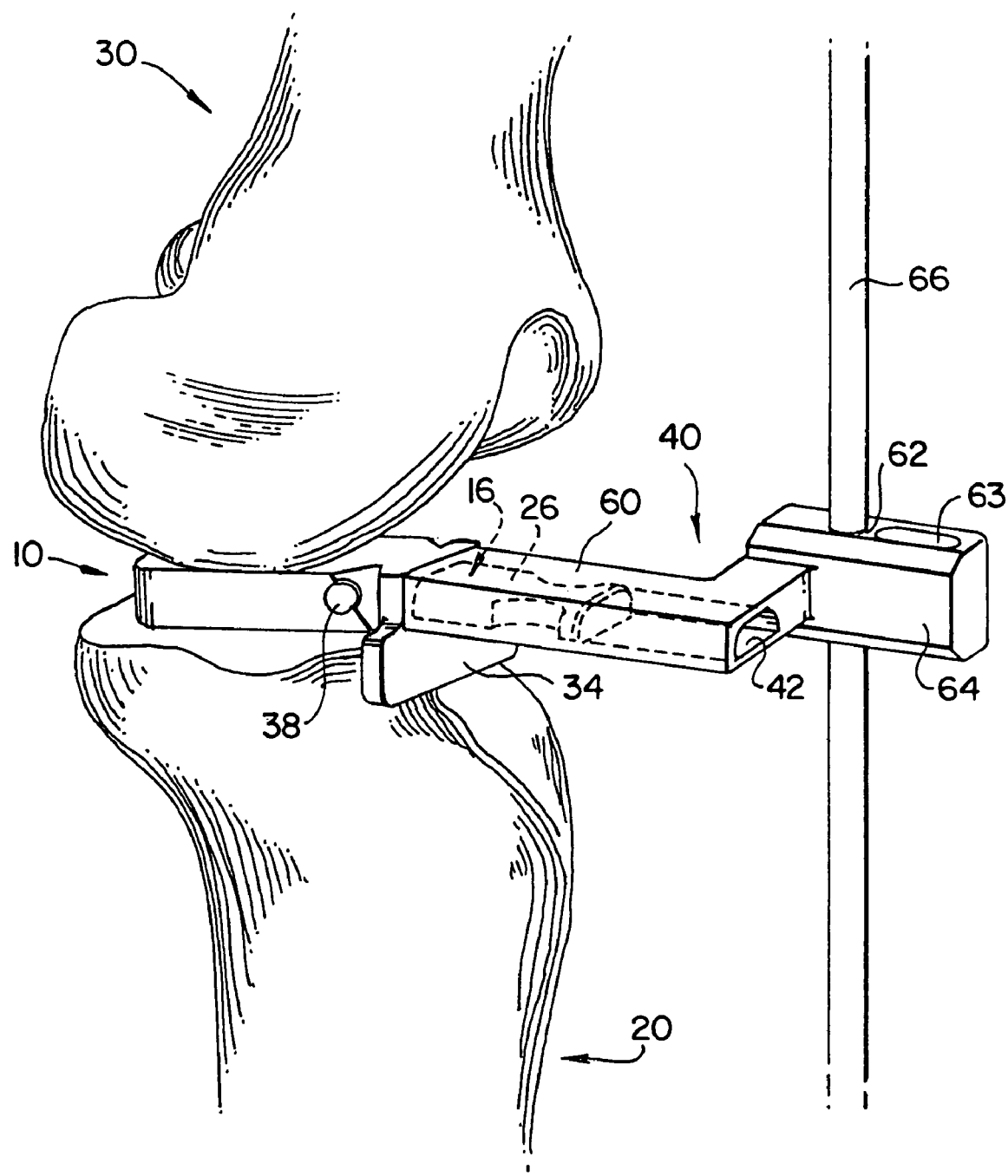
FIG. 7 is an enlarged view of the spacer block and alignment tower of FIG. 6, shown rotated approximately 45°.

Turning now to FIGS. 6 and 7, the attachment and use of alignment tower 40 will be described. Alignment tower 40 includes an attachment arrangement that is configured to mate with the attachment arrangement 16 of the spacer block 10. In this embodiment, the complementary attachment arrangement of the alignment tower consists of an aperture 42 of a generally D-shaped cross-section. Aperture 42 preferably extends the full length of the attachment arm 60 of the alignment tower. However, in order to better show the placement of projection 26 within aperture 42, some of the hidden lines representing the aperture 42 have been omitted.

This embodiment of alignment tower 40 includes other apertures, apertures 62 and 63, which each extend through rod arm 64. Apertures 62 and 63 are both configured to receive alignment rod 66, and either one may be used, depending upon the size of the patient's leg. As shown in FIG. 5, alignment rod 66 is aligned with the mechanical axis 54 of the femur 30 to verify that the spacer block (and subsequently the cuts for the femoral component) are properly aligned. If the alignment rod 66 does not align with the mechanical axis 54, a thicker or a thinner spacer block is substituted for the original spacer block, with such substitutions continuing until the desired alignment is achieved. If necessary, the proximal surface 12 of the tibia can also be re-cut in order to obtain the proper alignment. Once the alignment has been verified, the alignment tower 40 is removed from the spacer block 10.

Figure 8:
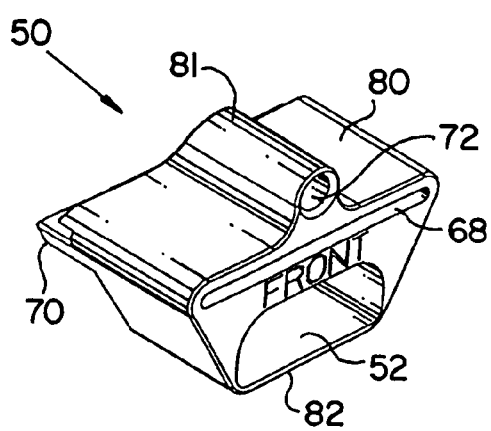
FIG. 8 is a proximal perspective view of an embodiment of a femoral cutting guide of the present invention.
Figure 9:
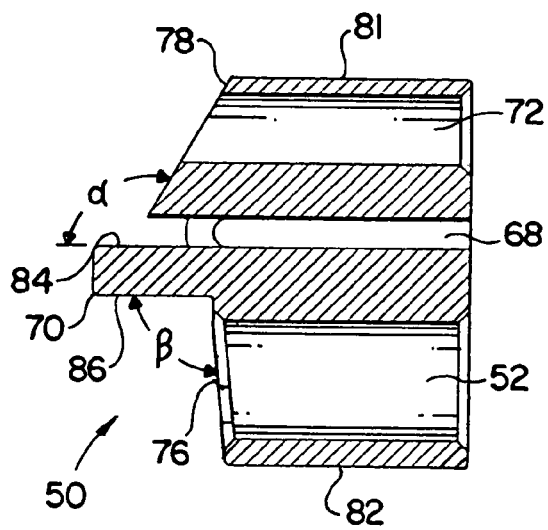
FIG. 9 is a cross-sectional side view of the femoral cutting guide of FIG. 8.
Figure 10:
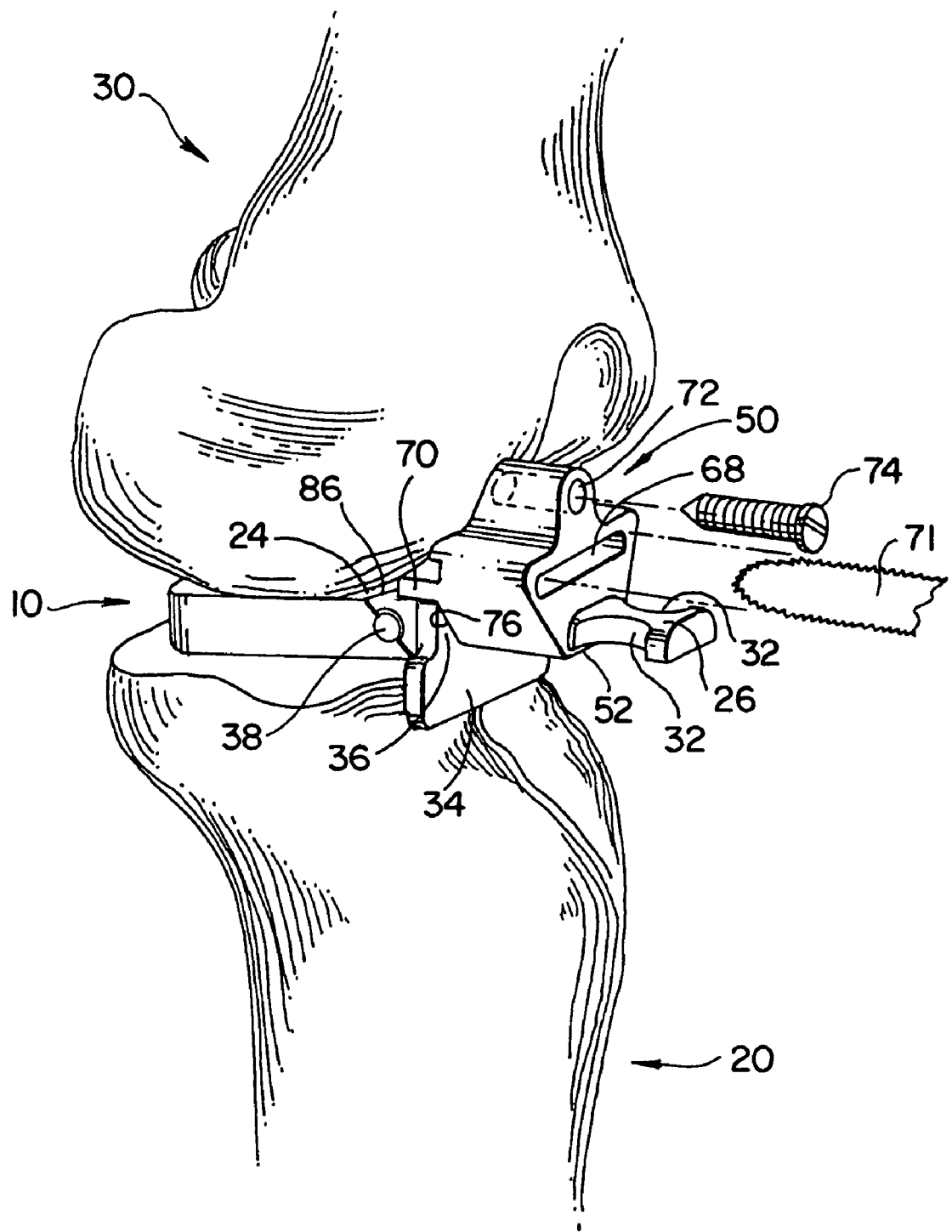
FIG. 10 is a view showing the femoral cutting guide of FIG. 8 attached to the spacer block of FIG. 1 and in position between a tibia and a femur.

Turning now to FIGS. 8 through 10, one embodiment of the femoral cutting guide 50 of the present invention will be described. FIG. 8 shows an anterior (or front) perspective view of femoral cutting guide 50, which is configured to be used for guiding a cutting blade when cutting the distal portion of one of the condyles (or for cutting the posterior portion of a condyle, when the limb is in flexion), and FIG. 9 shows a cross-section of the femoral cutting guide 50 of FIG. 8. FIG. 10 shows the femoral cutting guide in position, attached to the spacer block.

Femoral cutting guide 50 includes an attachment arrangement that is the complement of the attachment arrangement of the spacer block 10. In the embodiment of FIGS. 8-10, the attachment arrangement of guide 50 includes an aperture 52 that is of a generally D-shaped cross-section, which is configured to mate with projection 26 of the spacer block 10 (see FIG. 1). As mentioned above, other configurations of attachment arrangements are also contemplated as being within the scope of the invention.

Femoral cutting guide 50 also includes a slot that is configured to receive and guide a cutting member, such as blade 71 shown in FIG. 10. Blade 71 is attached to a reciprocating or oscillating saw (not shown), or other cutting device configured for use during knee arthroplasty.

Projecting from the posterior side of cutting guide 50 is a ledge 70, which is located distal of the slot 68 and proximal of aperture 52. Ledge 70 is configured to be seated above the proximal surface 24 of the main body portion 14 of the spacer block 10 (FIG. 1), with some clearance therebetween.

In order to maintain cutting guide 50 in position, an aperture 72 is preferably provided proximal of slot 68. Aperture 72, if provided, is used with a pin, such as pin 74 of FIG. 10. Although a threaded version of pin 74 is shown in FIG. 10, a non-threaded pin can also be used. In use, pin 74 is inserted through aperture 72, and into the femur 30, to more securely maintain cutting guide 50 in position.

Referring again to the embodiment of FIGS. 8 and 9, it can be seen that the distal posterior surface 76 and the proximal posterior surface 78 are not perpendicular to either the proximal surface 80 or the distal surface 82 (or to the outer aperture surface 81). Nor are distal posterior surface 76 and proximal posterior surface 78 perpendicular to proximal ledge surface 84 or to distal ledge surface 86, respectively. Instead, there is an angle αx between proximal posterior surface 78 and proximal ledge surface 84, and there is an angle β between distal ledge surface 86 and distal posterior surface 76. In this embodiment, angle αx is approximately 120° and angle β is approximately 95°. Of course, if desired, other angles may also be utilized. Angle α is provided to allow for cutting guide 50 to be seated as closely as possible with respect to the anterior condyle, and angle β is provided to allow the cutting guide to be seated as closely as possible with respect to the anterior side 36 of the main body portion 14 of the spacer block (FIG. 4). If there is a change in the angle that the anterior side of the main body portion of the spacer block makes with the projection 26, then angle β could also be changed accordingly.

In use, femoral cutting guide 50 is attached to the spacer block 10 as shown in FIG. 10. More specifically, the aperture 52 of the cutting guide 50 is mated with projection 26 of the spacer block 10 until the proximal posterior surface 78 contacts femur 30. The distal posterior surface 76 of the cutting guide 50 may make contact with the anterior side 36 of the main body portion 14 of the spacer block 10, or, preferably, there is a slight gap between these two surfaces. There is also preferably a slight gap between the distal ledge surface 86 of the cutting guide 50 and the proximal surface 24 of the spacer block 10. Additionally, at this point, the concave gripping areas 32 of projection 26 will be located completely outside of aperture 52.

As mentioned above, in this first embodiment, the projection 26 preferably includes two concave gripping areas 32, which facilitate gripping of the spacer block 10, as mentioned above. In order to enable adequate gripping of the spacer block 10 when the cutting guide 50 is attached thereto, preferably, at least about a third of the length of the projection 26 projects outwardly from the aperture 52, such as shown in FIG. 10.

If desired, pin 74 may be inserted through aperture 72 and into femur 30, to more securely maintain the femoral cutting guide 50 in the intended position. Next, slot 68 is used as a guide to guide blade 71 while cutting the distal condyle. After cutting of the distal condyle is completed, the cutting guide 50 is removed from the spacer block 10, and the spacer block is removed from its location.

Figure 11:
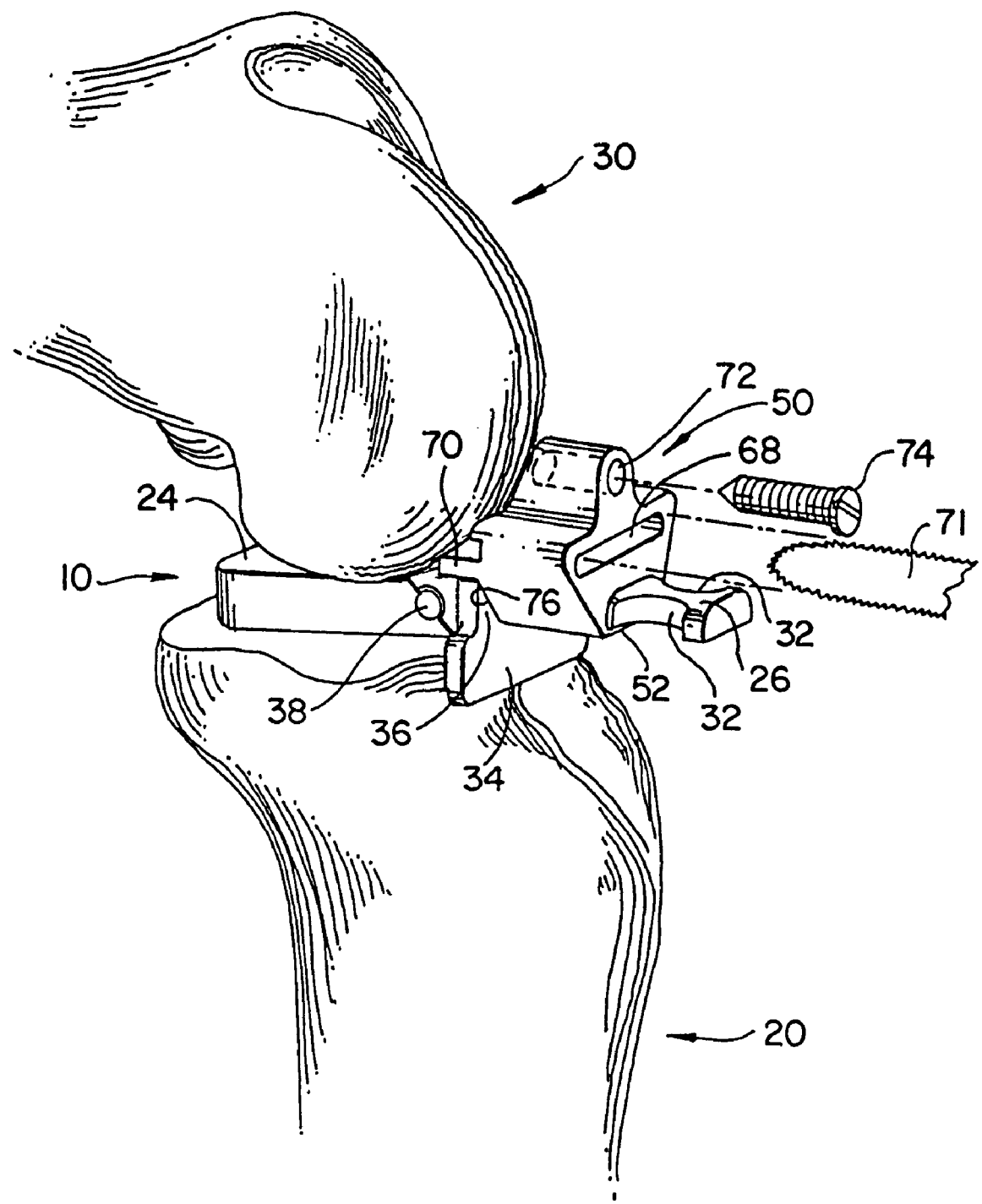
FIG. 11 is a view similar to FIG. 10, except showing the limb in flexion in order to enable the posterior femur to be cut.

As mentioned above, the present invention may also be used to cut the posterior condyle. FIG. 11 is a view similar to FIG. 10, except with the leg in flexion to enable the posterior condyle to be cut. The procedure for cutting the posterior condyle is essentially the same as that described above for cutting the distal condyle, except that the leg is in flexion, as shown in FIG. 11.

In order to finish the femur, any other cuts that need to be made, such as the posterior chamfer or drilling the holes for the pegs of the tibial component, can be made by any desired method. Likewise, the remainder of the procedure relating to 1I implanting a prosthetic knee also continues using any desired method.

Turning now to FIGS. 12-16, various alternate embodiments of the present invention are shown. Where appropriate, the same reference numbers as those used for the first embodiment will be used in these alternate embodiments, except for the addition of the prime designation. Unless otherwise noted, the embodiments of FIGS. 12-16 are used in the same manner as the first embodiment, and only the significant differences between these embodiments and the first embodiment will be described.

The embodiments of FIGS. 12-16 each include a spacer block 10' of a generally half-circular shape, as opposed to the generally rectangular shape of spacer block 10 of FIGS. 1-11. However, either shape, as well as other similar shapes, may be utilized in any of the embodiments. Further, although the drawing figures for the embodiments of FIGS. 12-16 only show the spacer blocks 10' and the femoral cutting guides 50', alignment towers should also be provided to cooperate with the spacer blocks 10'. Although the alignment towers for the embodiments of FIGS. 12-16 are not shown, the associated alignment towers will be essentially the same as alignment tower 40 of FIG. 7, except that the structure for attaching the alignment tower to the spacer block may not include apertures 42, but will instead include the same attachment arrangement found on the femoral cutting guide associated with each particular embodiment of spacer block.

Referring now to the embodiment of FIG. 12, this embodiment includes femoral cutting guide 50' and spacer block 10', which are configured to be attached to each other via an attachment arrangement and a complementary attachment arrangement that are different from the embodiment of FIGS.

1-11. More specifically, this embodiment includes one or more apertures 27 on spacer block 10' and corresponding projection(s) 53 on the femoral cutting guide 50'. It should be noted that although three aperture/projections sets are included in the example of this embodiment shown in FIG. 12, one, two, four or more projection/aperture sets can be provided if desired. Further, although the three aperture/projection sets are arranged in a generally triangular format with respect to each other (which prevents inverted assembly), such a configuration is not required, because other configurations, including those that do not prevent inverted assembly, are also contemplated as being within the scope of the invention.

Another difference between this embodiment and the embodiment of FIGS. 1-11 is that the femoral cutting guide 50' is a bit larger than cutting guide 50 of the first embodiment, and it also includes more apertures 72' than that single aperture 72 shown in FIGS. 8 and 9. The use of more apertures in this embodiment provides the surgeon with more options for placement of one or more pins (such as pin 74 of FIG. 10), while the single aperture configuration of the first embodiment provides a more compact guide that requires less material to manufacture. Of course, any of the embodiments can be made with either a single aperture or with multiple apertures.

Additionally, the spacer block 10' shown in FIG. 12 lacks an anterior stop (such as anterior stop 34 shown in FIGS. 1-5). If desired, apertures (not shown) can be added to spacer block 10' to be used with pins maintain the spacer block in position upon the tibia, or the spacer block can simply be held in position. Additionally, any other means of maintaining the spacer block in position can also be used.

Figure 13A:
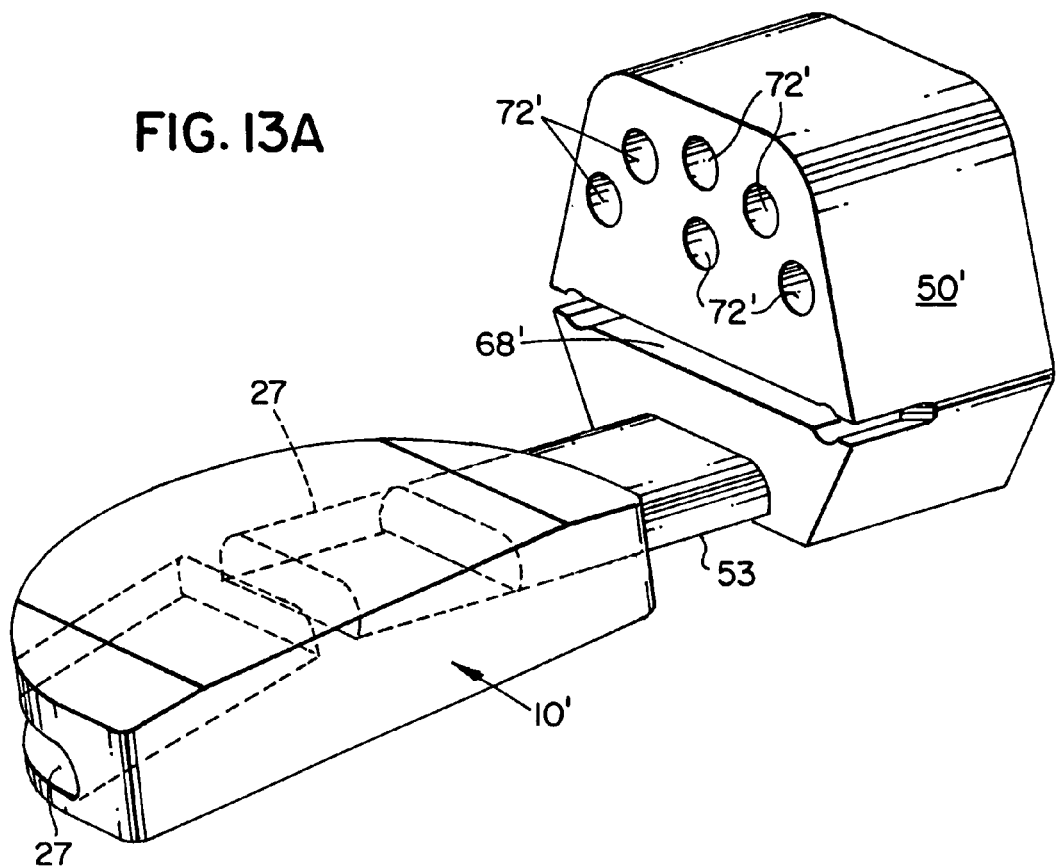
FIGS. 13A and 13B are views of a spacer block and a cutting guide of a third embodiment of the present invention, where
Figure 13B:
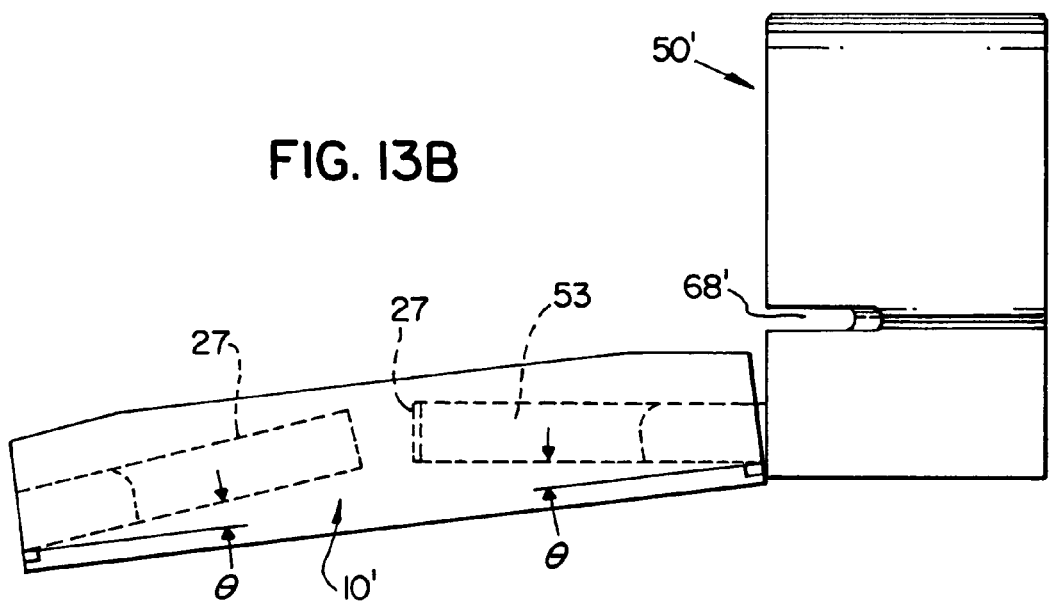

The embodiment of FIGS. 13A and 13B is very similar to the FIG. 12 embodiment, except this embodiment utilizes a single generally D-shaped projection 53 that mates with a single generally D-shaped aperture 27. The attachment arrangements of this embodiment differ from the generally D-shaped attachment arrangements of the embodiment of FIGS. 1-11 by being reversed (i.e., in the FIG. 13A/13B embodiment, the projection is on the femoral cutting guide and the aperture is on the spacer block, while in the embodiment of FIGS. 1-11 the projection is on the spacer block and the aperture is on the femoral cutting guide).

Figure 14A:
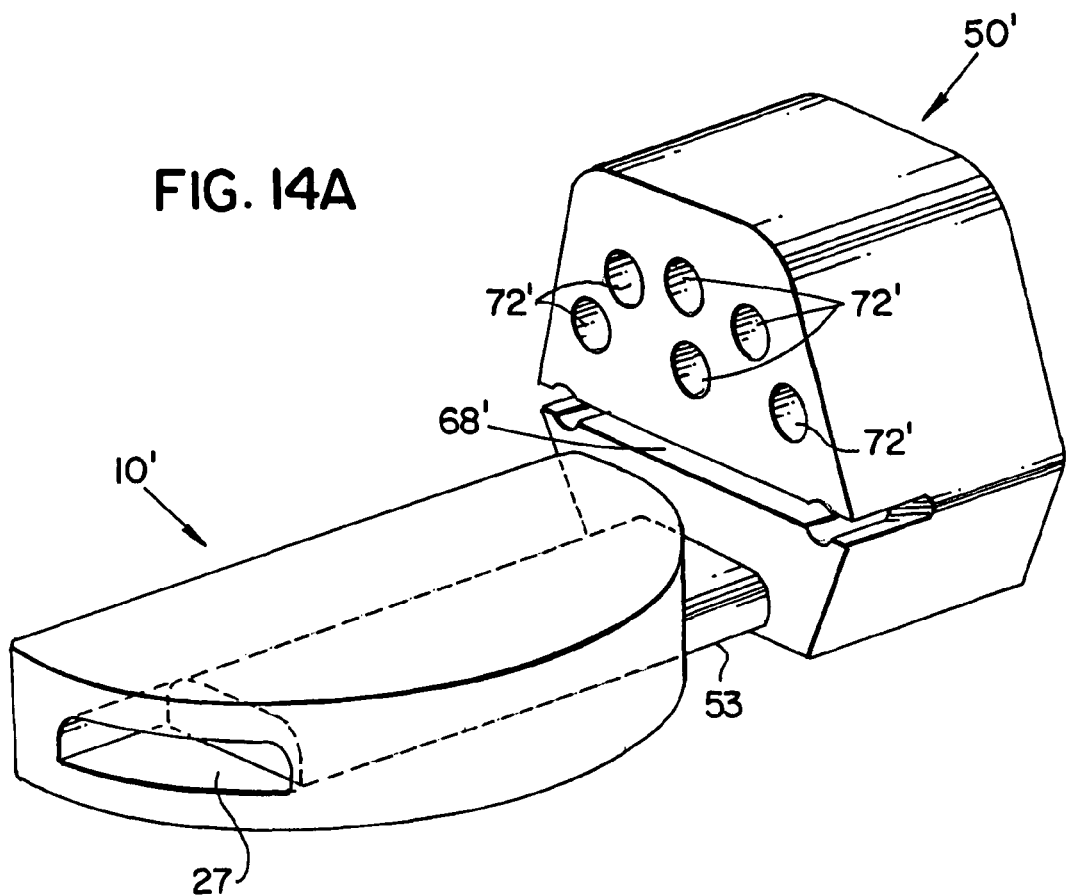
FIGS. 14A and 14B are views of a spacer block and a cutting guide of a fourth embodiment of the present invention, where
Figure 14B:
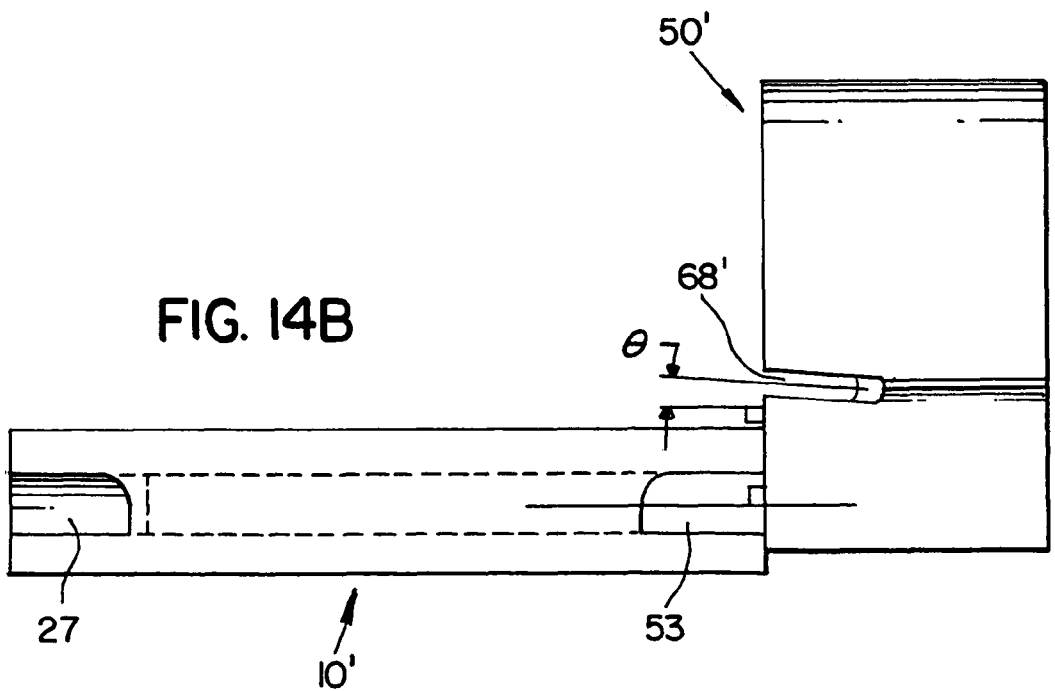

The embodiment of FIGS. 14A and 14B is very similar to the embodiment of FIGS. 13A and 13B, except with regard to the manner in which the posterior tibial slope is accounted for. In the first embodiment of FIGS. 1-11, as well as in the second embodiment of FIG. 12 and the third embodiment of FIGS. 13A/13B, the posterior tibial slope is accounted for by angling the portion of the attachment arrangement found on the spacer block with respect to the generally parallel attachment arrangement and cutting slot on the cutting guide. For example, in the first embodiment, FIG. 4 shows how the projection 26 of the attachment arrangement of the spacer block 10 is offset by angle θ, while FIG. 9 shows that the cutting slot 68 and the aperture 52 of the attachment arrangement of femoral cutting guide 50 are generally parallel to each other, and are not offset. Similarly, the embodiment of FIGS. 13A and 13B includes apertures 27 that are offset, while projections 53 are not offset, and are generally parallel with cutting slot 68', as best shown in FIG. 13B.

In contrast, in the embodiment of FIGS. 14A and 14B, the apertures 27 are not offset, nor are projections 53, as best shown in FIG. 14B, but instead the cutting slot 68' is offset by angle θ with respect to projection 53. Angle θ is the same angle θ defined with respect to FIG. 4, and therefore it is preferably 5°, although other angles may also be used, such as any angle between 0° and 10°, and more preferably any angle between 3° and 7°. The alternate arrangement for accounting for the posterior tibial slope described in this embodiment may be substituted for the arrangement provided for in any of the other embodiments.

Figure 15A:
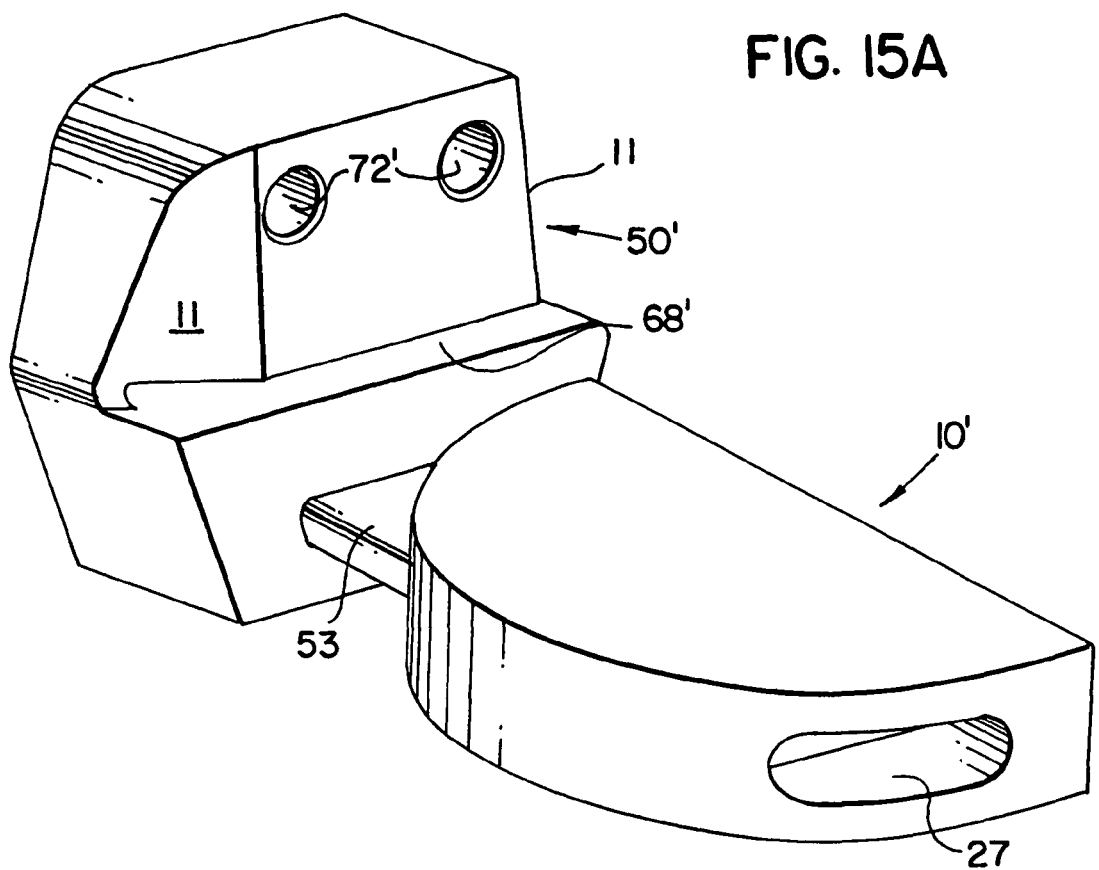
FIGS. 15A and 15B are views of a spacer block and a cutting guide of a fifth embodiment of the present invention, where
Figure 15B:
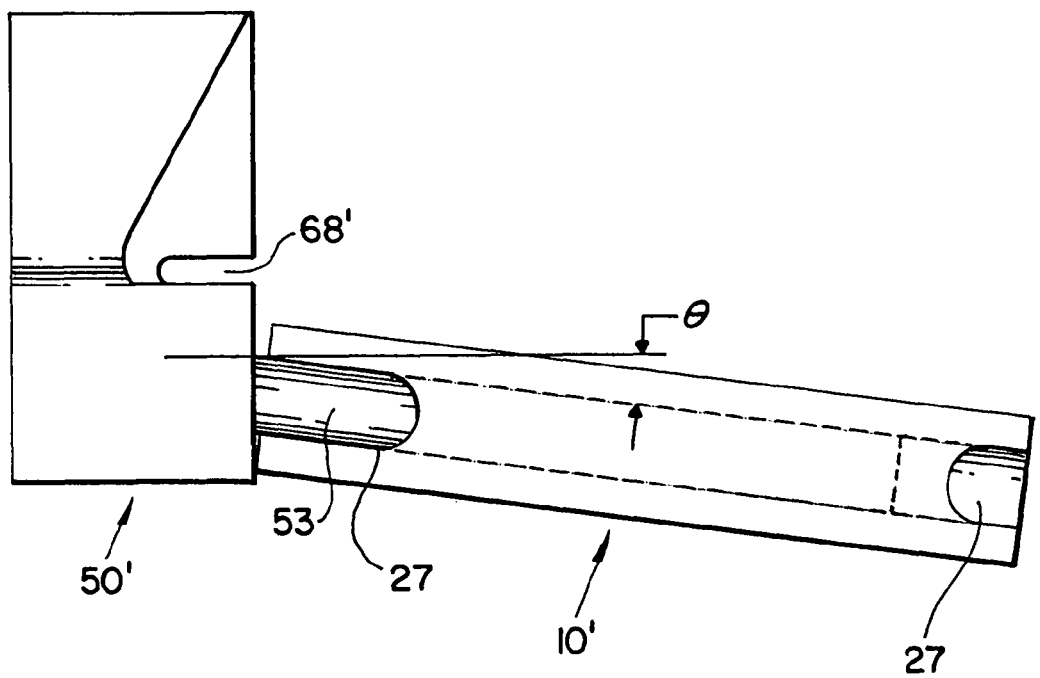

The embodiment of FIGS. 15A and 15B includes another different arrangement for accounting for the posterior tibial slope. In this embodiment, as best seen in FIG. 15B, the projection 53 extending from the femoral cutting guide 50' is offset by angle θ, while the apertures 27 of the spacer block 10 and the cutting slot 68' are not offset. Once again, this further alternate arrangement for accounting for the posterior tibial slope may also be substituted for the arrangement provided for in any of the other embodiments. In general, the posterior tibial slope may be accounted for by providing an offset in the attachment arrangement of the spacer block (whether projection(s) or aperture(s)) or by providing the offset in the attachment arrangement of the femoral cutting guide and alignment tower (whether projection(s) or aperture(s)), or it may be accounted for by provided the offset in the cutting slot.

The FIG. 15A/15B embodiment also includes another feature not shown on the other embodiments, but which can be included in most of the other embodiments if desired—chamfers 11. (Chamfers 11 are not necessary in the first embodiment (FIGS. 8 and 9) because no excess material is provided adjacent the aperture 72.) The pair of chamfers 11 may optionally be provided on the femoral cutting guide 50' in order to reduce the material required to manufacture guide 50', and also to avoid potential obstructions caused by portions of a particular femur, which may otherwise hinder a close relationship between the cutting guide and the femur.

Figure 16:
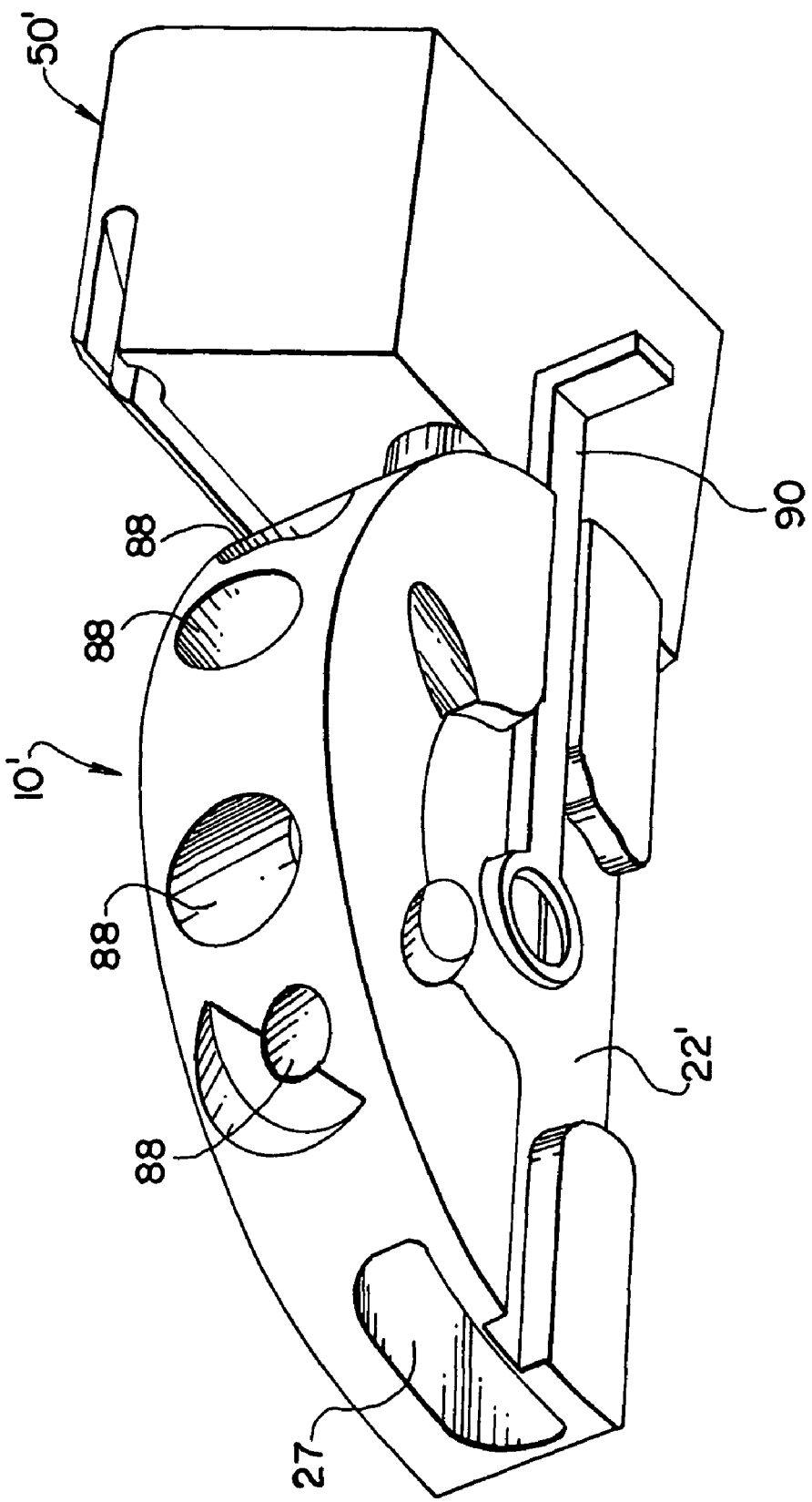
FIG. 16 is a perspective view of a spacer block and a cutting guide of a sixth embodiment of the present invention.

An additional embodiment is shown in FIG. 16. The femoral cutting guide 50' of this embodiment is essentially the same as the femoral cutting guide 50 shown in FIGS. 8 and 9 of the first embodiment, except that the attachment arrangement is a generally D-shaped projection (as opposed to the generally D-shaped aperture 52 of FIGS. 8 and 9). Thus, the male and female portions of the attachment arrangements of this embodiment are reversed when compared with the first embodiment. However, as mentioned above, other attachment arrangements can be substituted for those shown in a specific embodiment.

Other than the type of attachment arrangement, the spacer block 10' of FIG. 16 is essentially the same as those of the embodiments of FIGS. 12-15, except this embodiment also includes a plurality of additional apertures 88 and a modular hook 90. The additional apertures 88, which are optional in this embodiment and which can be added to any of the other embodiments, are provided to allow the surgeon to pin the spacer block to the tibia. In use, a pin (such as pin 58 of FIG. 5) is inserted into one or more of the apertures 88 to maintain the spacer block in position upon the tibia. Modular hook 90 performs the same function as anterior stop 34 shown in FIGS. 1-5. Accordingly, modular hook 90 may be used instead of anterior stop 34 in the first embodiment, and it may be added to any of the other embodiments as well. In the example of modular hook 90 shown in FIG. 15, hook 90 is secured to the distal surface 22' of the spacer block 10' via a screw, or other easily removably attachment means. Accordingly, the modular hook 90 can easily be repositioned on the opposite side of the spacer block when the other aperture 27 is mated with the projection 53. Additionally, distal surface 22' preferably includes a recessed portion 23 to allow the spacer block 10' to sit in a relatively flat manner upon the resected proximal surface of the tibia when the hook 90 is in position.

While various embodiments of the present invention have been shown and described, it should be understood that other modifications, substitutions and alternatives may be apparent to one of ordinary skill in the art. Such modifications, substitutions and alternatives can be made without departing from the spirit and scope of the invention, which should be determined from the appended claims.

What is claimed is:

1. In combination, a tibial component of a knee prosthesis and a system of components used during knee arthroplasty, after resection of a tibia, for guiding a cutting member into proper orientation for resecting a portion of a femur, said combination comprising:

the tibial component having a thickness;

the system comprising:
- a femoral cutting guide including a slot configured and arranged to receive a cutting member intended to resect a portion of the femur; and
- a plurality of spacer blocks of different predefined thicknesses, each configured to be temporarily positioned upon a resected proximal portion of a tibia during knee arthroplasty, either with or without a modular attachment attached thereto, each of said spacer blocks including:
  - a main body portion having said predefined thickness defined between substantially parallel distal and proximal surfaces, wherein said predefined thickness of said main body portion of a particular spacer block is approximately equal to said thickness of said tibial component of a knee joint prosthesis;
  - an attachment arrangement on an anterior side of said main body portion, wherein said attachment arrangement is configured and arranged to mate with a complementary attachment arrangement on said femoral cutting guide; and
  - an anterior stop projecting from said distal surface of said spacer block, near said anterior side, wherein said anterior stop is configured and arranged to contact an anterior edge of a tibia when said spacer block is positioned upon the resected proximal portion of a tibia in order to prevent movement of said spacer block in a posterior direction.

2. The combination as defined in claim 1, wherein said slot on said cutting guide is configured and arranged to guide the cutting member for cutting distal portions of medial and lateral condyles.

3. The combination as defined in claim 1, further comprising:
- an alignment tower including a second complementary attachment arrangement, of a similar configuration to said complementary attachment arrangement of said femoral cutting guide, wherein said second complementary attachment arrangement is also configured and arranged to mate with said attachment arrangement of each of said spacer blocks; and
- an alignment rod configured to be inserted into a hole within said alignment tower, wherein said alignment rod is used for verifying the alignment of a mechanical axis of a limb when said spacer block is positioned between the tibia and the femur.

4. The combination as defined in claim 1, wherein:
- said attachment arrangement of each of said spacer blocks includes either at least one projection or at least one aperture; and
- said complementary attachment arrangement of said femoral cutting guide includes the other of at least one projection or at least one aperture, depending upon a configuration of said attachment arrangement of said spacer blocks, so that said attachment arrangement can mate with said complementary attachment arrangement.

5. The combination as defined in claim 1, wherein:
- said attachment arrangement of said spacer block includes at least one projection; and
- said complementary attachment arrangement of said femoral cutting guide includes at least one aperture configured to receive said at least one projection.

6. The combination as defined in claim 5, wherein when said at least one projection of said spacer block is mated with said at least one aperture of said femoral cutting guide, at least a third of a length of said at least one projection projects outwardly of said at least one aperture.

7. The combination as defined in claim 5, wherein a proximal surface of said at least one projection of said attachment arrangement of said spacer block is offset with respect to said proximal surface of said main body portion of each of said spacer blocks.

8. The combination as defined in claim 7, where said offset is approximately 5°.

9. The combination as defined in claim 5, wherein said at least one projection of said spacer block is of a generally D-shaped cross-section, and said at least one aperture of said femoral cutting guide is of a generally D-shaped cross-section.

10. The combination as defined in claim 5, wherein said projection of said spacer block includes two concave gripping areas, whereby said two concave gripping areas facilitate gripping of said spacer block.

11. The combination as defined in claim 1, wherein one of said attachment arrangement of said spacer blocks, said complementary attachment arrangement of said femoral cutting guide, or said slot of said femoral cutting guide is offset to account for posterior tibial slope.

12. The combination as defined in claim 1, wherein said attachment arrangement of said spacer block is configured and arranged to prevent inverted attachment of said complementary attachment arrangement with said attachment arrangement of said spacer block.

13. The combination as defined in claim 1, wherein:
- said spacer block includes means for temporarily positioning said spacer block upon either a lateral portion or a medial portion of the resected proximal portion of the tibia; and
- said spacer block is configured and arranged to be positioned into knee joint spaces in right legs and in left legs.

14. The combination as defined in claim 13, wherein said means for temporarily positioning said spacer block includes at least one aperture configured to accept a pin for pinning said spacer block into position upon the resected proximal portion of the tibia.

15. The combination as defined in claim 13, wherein said means for temporarily positioning said spacer block includes said anterior stop projecting from said distal surface of said spacer block.

16. The combination as defined in claim 15, wherein said means for temporarily positioning said spacer block also includes at least one aperture configured to accept a pin for pinning said spacer block into position upon the resected proximal portion of the tibia.

17. The combination as defined in claim 3, wherein:
- said attachment arrangement of said spacer block includes at least one projection; and
- said second complementary attachment arrangement of said alignment tower includes at least one aperture configured to receive said at least one projection of said spacer block.

18. The combination as defined in claim 17, wherein said at least one projection of said spacer block is of a generally D-shaped cross-section, and said at least one aperture of said alignment tower is of a generally D-shaped cross-section.

* * * * *